US008288372B2

(12) United States Patent
Hale et al.

(10) Patent No.: US 8,288,372 B2
(45) Date of Patent: *Oct. 16, 2012

(54) METHOD FOR TREATING HEADACHE WITH LOXAPINE

(75) Inventors: Ron L. Hale, Woodside, CA (US); Patrik Munzar, Belmont, CA (US); Joshua D. Rabinowitz, Mountain View, CA (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 1104 days.

This patent is subject to a terminal disclaimer.

(21) Appl. No.: 10/719,540

(22) Filed: Nov. 20, 2003

(65) Prior Publication Data
US 2004/0102434 A1 May 27, 2004

Related U.S. Application Data

(60) Provisional application No. 60/429,405, filed on Nov. 26, 2002.

(51) Int. Cl.
*A61K 31/553* (2006.01)
*A61K 31/55* (2006.01)

(52) U.S. Cl. ......... 514/211.13; 514/211.01; 514/211.11; 514/211.15; 514/217

(58) Field of Classification Search ............. 514/211.01, 514/211.11, 211.13, 211.15, 217
See application file for complete search history.

(56) References Cited

U.S. PATENT DOCUMENTS

| 2,902,484 A | 9/1959 | Horclois |
| 3,219,533 A | 11/1965 | Mullins |
| 3,546,226 A | 12/1970 | Hunzikor et al. |
| 3,560,607 A | 2/1971 | Hartley et al. |
| 3,949,743 A | 4/1976 | Shanbrom |
| 3,982,095 A | 9/1976 | Robinson |
| 4,141,369 A | 2/1979 | Burruss |
| 4,183,912 A | 1/1980 | Rosenthale |
| RE30,285 E | 5/1980 | Babington |
| 4,303,083 A | 12/1981 | Burruss, Jr. |
| 4,474,191 A | 10/1984 | Steiner |
| 4,484,576 A | 11/1984 | Albarda |
| 4,566,451 A | 1/1986 | Badewien |
| 4,603,132 A | 7/1986 | Subissi |
| 4,708,151 A | 11/1987 | Shelar |
| 4,734,560 A | 3/1988 | Bowen |
| 4,735,217 A | 4/1988 | Gerth et al. |
| 4,819,665 A | 4/1989 | Roberts et al. |
| 4,848,374 A | 7/1989 | Chard et al. |
| 4,853,517 A | 8/1989 | Bowen et al. |
| 4,895,719 A | 1/1990 | Radhakrishnan et al. |
| 4,906,417 A | 3/1990 | Gentry |
| 4,917,119 A | 4/1990 | Potter et al. |
| 4,924,883 A | 5/1990 | Perfetti et al. |
| 4,941,483 A | 7/1990 | Ridings et al. |
| 4,963,289 A | 10/1990 | Ortiz et al. |
| 5,042,509 A | 8/1991 | Banerjee et al. |
| 5,049,389 A | 9/1991 | Radhakrishnan |
| 5,060,671 A | 10/1991 | Counts et al. |
| 5,099,861 A | 3/1992 | Clearman et al. |
| 5,135,009 A | 8/1992 | Muller et al. |
| 5,144,962 A | 9/1992 | Counts et al. |
| 5,146,915 A | 9/1992 | Montgomery |
| 5,224,498 A | 7/1993 | Deevi et al. |
| 5,284,133 A * | 2/1994 | Burns et al. ............. 128/200.23 |
| 5,345,951 A | 9/1994 | Serrano et al. |
| 5,364,838 A | 11/1994 | Rubsamen |
| 5,366,770 A | 11/1994 | Wang |
| 5,388,574 A | 2/1995 | Ingebrethsen |
| 5,431,167 A | 7/1995 | Savord |
| 5,456,247 A | 10/1995 | Shilling et al. |
| 5,511,726 A | 4/1996 | Greenspan et al. |
| 5,522,385 A | 6/1996 | Lloyd et al. |
| 5,564,442 A | 10/1996 | MacDonald et al. |
| 5,592,934 A | 1/1997 | Thwaites |
| 5,605,146 A | 2/1997 | Sarela |
| 5,649,554 A | 7/1997 | Sprinkel et al. |
| 5,666,977 A | 9/1997 | Higgins et al. |
| 5,694,919 A | 12/1997 | Rubsamen et al. |
| 5,699,789 A | 12/1997 | Hendricks |
| 5,735,263 A | 4/1998 | Rubsamen et al. |
| 5,738,865 A | 4/1998 | Baichwal et al. |
| 5,743,251 A | 4/1998 | Howell et al. |
| 5,758,637 A | 6/1998 | Ivri et al. |
| 5,819,756 A | 10/1998 | Mielordt |
| 5,840,246 A | 11/1998 | Hammons et al. |
| 5,855,913 A | 1/1999 | Hanes et al. |
| 5,874,481 A | 2/1999 | Weers et al. |

(Continued)

FOREIGN PATENT DOCUMENTS

| CH | 436 297 A | 5/1967 |
| EP | 0 358 114 | 3/1990 |
| EP | 0 606 486 | 7/1994 |
| EP | 1 080 720 | 3/2001 |
| GB | 502 761 | 1/1938 |
| WO | WO 94/09842 | 5/1994 |
| WO | WO 96/09846 | 4/1996 |
| WO | WO 96/13161 | 5/1996 |
| WO | WO 96/13290 | 5/1996 |
| WO | WO 96/13291 | 5/1996 |

(Continued)

OTHER PUBLICATIONS

Drug Information Handbook, 2nd edition, Lexi-Comp, Inc.: Cleveland, 1994-1995, pp. 554-555.*
McGee et al. (1979) "Phenotiazine Analgesia—Fact or Fantasy?" *American Journal of Hospital Pharmacy* vol. 36: 633-640.
Magnusson et al. (2000) "The Involvement of Dopamine in Nociception: the role of D1 and D2 Receptors in the Dorsolateral Striatum." *Brain Research* vol. 855: 260-266.

(Continued)

*Primary Examiner* — James H. Alstrum-Acevedo
(74) *Attorney, Agent, or Firm* — Swanson & Bratschun, L.L.C.

(57) ABSTRACT

Loxapine, amoxapine, or salts or prodrugs of either, is effective in alleviating pain, particularly headache pain such as migraine, cluster headaches and tension headaches. Preferably the loxapine or amoxapine is administered systemically, most preferably by inhalation.

16 Claims, 2 Drawing Sheets

U.S. PATENT DOCUMENTS

| | | | |
|---|---|---|---|
| 5,875,776 A | 3/1999 | Vaghefi | |
| 5,884,620 A | 3/1999 | Gonda et al. | |
| 5,891,885 A | 4/1999 | Caruso | |
| 5,894,841 A | 4/1999 | Voges | |
| 5,900,249 A | 5/1999 | Smith | |
| 5,915,378 A | 6/1999 | Lloyd et al. | |
| 5,918,595 A | 7/1999 | Olsson | |
| 5,929,070 A | 7/1999 | Shannon et al. | |
| 5,934,272 A | 8/1999 | Lloyd et al. | |
| 5,941,240 A | 8/1999 | Gonda et al. | |
| 5,945,416 A | 8/1999 | Shannon et al. | |
| 5,957,124 A | 9/1999 | Lloyd et al. | |
| 5,960,792 A | 10/1999 | Lloyd et al. | |
| 5,993,805 A | 11/1999 | Sutton et al. | |
| 6,041,777 A | 3/2000 | Faithfull et al. | |
| 6,051,566 A | 4/2000 | Bianco | |
| 6,090,212 A | 7/2000 | Mahawili | |
| 6,095,134 A | 8/2000 | Sievers et al. | |
| 6,095,153 A | 8/2000 | Kessler et al. | |
| 6,102,036 A | 8/2000 | Slutsky et al. | |
| 6,131,570 A | 10/2000 | Schuster et al. | |
| 6,136,295 A | 10/2000 | Edwards et al. | |
| 6,150,353 A | 11/2000 | Broekkamp et al. | |
| 6,155,268 A | 12/2000 | Takeuchi | |
| 6,158,431 A | 12/2000 | Poole | |
| 6,167,880 B1 | 1/2001 | Gonda et al. | |
| 6,211,171 B1 | 4/2001 | Sawynok et al. | |
| 6,234,167 B1 | 5/2001 | Cox et al. | |
| 6,241,969 B1 | 6/2001 | Saidi et al. | |
| 6,250,289 B1 | 6/2001 | Esteghlal et al. | |
| 6,255,334 B1 | 7/2001 | Sands | |
| 6,258,807 B1 | 7/2001 | Helton et al. | |
| 6,290,986 B1 | 9/2001 | Murdock et al. | |
| 6,299,900 B1 | 10/2001 | Reed et al. | |
| 6,376,550 B1 | 4/2002 | Raber et al. | |
| 6,408,854 B1 | 6/2002 | Gonda et al. | |
| 6,431,166 B2 | 8/2002 | Gonda et al. | |
| 6,444,665 B1 | 9/2002 | Helton et al. | |
| 6,461,591 B1 | 10/2002 | Keller et al. | |
| 6,479,074 B2 | 11/2002 | Murdock et al. | |
| 6,506,762 B1 | 1/2003 | Horvath et al. | |
| 6,514,482 B1 | 2/2003 | Bartus et al. | |
| 6,591,839 B2 | 7/2003 | Meyer et al. | |
| 6,632,047 B2 | 10/2003 | Vinegar et al. | |
| 6,638,981 B2 | 10/2003 | Williams et al. | |
| 6,682,716 B2 | 1/2004 | Hodges et al. | |
| 6,701,922 B2 | 3/2004 | Hindle et al. | |
| 6,716,415 B2 | 4/2004 | Rabinowitz et al. | |
| 6,716,416 B2 | 4/2004 | Rabinowitz et al. | |
| 6,716,417 B2 | 4/2004 | Rabinowitz et al. | |
| 6,737,042 B2 | 5/2004 | Rabinowitz et al. | |
| 6,737,043 B2 | 5/2004 | Rabinowitz et al. | |
| 6,740,307 B2 | 5/2004 | Rabinowitz et al. | |
| 6,740,308 B2 | 5/2004 | Rabinowitz et al. | |
| 6,740,309 B2 | 5/2004 | Rabinowitz et al. | |
| 6,743,415 B2 | 6/2004 | Rabinowitz et al. | |
| 6,759,029 B2 | 7/2004 | Hale et al. | |
| 6,772,756 B2 | 8/2004 | Shayan | |
| 6,776,978 B2 | 8/2004 | Rabinowitz et al. | |
| 6,780,399 B2 | 8/2004 | Rabinowitz et al. | |
| 6,780,400 B2 | 8/2004 | Rabinowitz et al. | |
| 6,783,753 B2 | 8/2004 | Rabinowitz et al. | |
| 6,797,259 B2 | 9/2004 | Rabinowitz et al. | |
| 6,803,031 B2 | 10/2004 | Rabinowitz et al. | |
| 6,805,853 B2 | 10/2004 | Rabinowitz et al. | |
| 6,805,854 B2 | 10/2004 | Hale et al. | |
| 6,814,954 B2 | 11/2004 | Rabinowitz et al. | |
| 6,814,955 B2 | 11/2004 | Rabinowitz et al. | |
| 6,855,310 B2 | 2/2005 | Rabinowitz et al. | |
| 6,884,408 B2 | 4/2005 | Rabinowitz et al. | |
| 6,994,843 B2 | 2/2006 | Rabinowitz et al. | |
| 7,005,121 B2 | 2/2006 | Rabinowitz et al. | |
| 7,005,122 B2 | 2/2006 | Hale et al. | |
| 7,008,615 B2 | 3/2006 | Rabinowitz et al. | |
| 7,008,616 B2 | 3/2006 | Rabinowitz et al. | |
| 7,011,819 B2 | 3/2006 | Hale et al. | |
| 7,011,820 B2 | 3/2006 | Rabinowitz et al. | |
| 7,014,840 B2 | 3/2006 | Hale et al. | |
| 7,014,841 B2 | 3/2006 | Rabinowitz et al. | |
| 7,018,619 B2 | 3/2006 | Rabinowitz et al. | |
| 7,018,620 B2 | 3/2006 | Rabinowitz et al. | |
| 7,018,621 B2 | 3/2006 | Hale et al. | |
| 7,022,312 B2 | 4/2006 | Rabinowitz et al. | |
| 7,029,658 B2 | 4/2006 | Rabinowitz et al. | |
| 7,033,575 B2 | 4/2006 | Rabinowitz et al. | |
| 7,040,314 B2 * | 5/2006 | Nguyen et al. | 128/203.12 |
| 7,045,118 B2 | 5/2006 | Rabinowitz et al. | |
| 7,045,119 B2 | 5/2006 | Rabinowitz et al. | |
| 7,048,909 B2 | 5/2006 | Rabinowitz et al. | |
| 7,052,679 B2 | 5/2006 | Rabinowitz et al. | |
| 7,052,680 B2 | 5/2006 | Rabinowitz et al. | |
| 7,060,254 B2 | 6/2006 | Rabinowitz et al. | |
| 7,060,255 B2 | 6/2006 | Rabinowitz et al. | |
| 7,063,830 B2 | 6/2006 | Rabinowitz et al. | |
| 7,063,831 B2 | 6/2006 | Rabinowitz et al. | |
| 7,063,832 B2 | 6/2006 | Rabinowitz et al. | |
| 7,067,114 B2 | 6/2006 | Rabinowitz et al. | |
| 7,070,761 B2 | 7/2006 | Rabinowitz et al. | |
| 7,070,762 B2 | 7/2006 | Rabinowitz et al. | |
| 7,070,763 B2 | 7/2006 | Rabinowitz et al. | |
| 7,070,764 B2 | 7/2006 | Rabinowitz et al. | |
| 7,070,765 B2 | 7/2006 | Rabinowitz et al. | |
| 7,070,766 B2 | 7/2006 | Rabinowitz et al. | |
| 7,078,016 B2 | 7/2006 | Rabinowitz et al. | |
| 7,078,017 B2 | 7/2006 | Rabinowitz et al. | |
| 7,078,018 B2 | 7/2006 | Rabinowitz et al. | |
| 7,078,019 B2 | 7/2006 | Rabinowitz et al. | |
| 7,078,020 B2 | 7/2006 | Rabinowitz et al. | |
| 7,087,216 B2 | 8/2006 | Rabinowitz et al. | |
| 7,087,217 B2 | 8/2006 | Rabinowitz et al. | |
| 7,087,218 B2 | 8/2006 | Rabinowitz et al. | |
| 7,090,830 B2 | 8/2006 | Hale et al. | |
| 7,094,392 B2 | 8/2006 | Rabinowitz et al. | |
| 7,108,847 B2 | 9/2006 | Rabinowitz et al. | |
| 7,115,250 B2 | 10/2006 | Rabinowitz et al. | |
| 7,169,378 B2 | 1/2007 | Rabinowitz et al. | |
| 7,402,777 B2 | 7/2008 | Ron et al. | |
| 2001/0020147 A1 | 9/2001 | Staniforth et al. | |
| 2002/0037828 A1 | 3/2002 | Wilson et al. | |
| 2002/0058009 A1 | 5/2002 | Bartus et al. | |
| 2002/0086852 A1 | 7/2002 | Cantor et al. | |
| 2002/0112723 A1 | 8/2002 | Schuster et al. | |
| 2002/0117175 A1 | 8/2002 | Kottayil et al. | |
| 2002/0176841 A1 | 11/2002 | Barker et al. | |
| 2003/0004142 A1 | 1/2003 | Prior et al. | |
| 2003/0015196 A1 | 1/2003 | Hodges et al. | |
| 2003/0015197 A1 | 1/2003 | Hale et al. | |
| 2003/0032638 A1 | 2/2003 | Kim et al. | |
| 2003/0051728 A1 | 3/2003 | Lloyd et al. | |
| 2003/0062042 A1 | 4/2003 | Wensley et al. | |
| 2003/0118512 A1 | 6/2003 | Shen | |
| 2003/0131843 A1 | 7/2003 | Lu | |
| 2003/0138508 A1 | 7/2003 | Novack et al. | |
| 2003/0209240 A1 | 11/2003 | Hale et al. | |
| 2003/0215119 A1 | 11/2003 | Hale et al. | |
| 2004/0009128 A1 * | 1/2004 | Rabinowitz et al. | 424/46 |
| 2004/0016427 A1 | 1/2004 | Byron et al. | |
| 2004/0096402 A1 | 5/2004 | Hodges et al. | |
| 2004/0099266 A1 | 5/2004 | Cross et al. | |
| 2004/0101481 A1 | 5/2004 | Hale et al. | |
| 2004/0105818 A1 | 6/2004 | Every et al. | |
| 2004/0105819 A1 | 6/2004 | Hale et al. | |
| 2004/0234699 A1 | 11/2004 | Hale et al. | |
| 2004/0234914 A1 | 11/2004 | Hale et al. | |
| 2004/0234916 A1 | 11/2004 | Hale et al. | |
| 2005/0034723 A1 | 2/2005 | Bennett et al. | |
| 2005/0037506 A1 | 2/2005 | Hale et al. | |
| 2005/0079166 A1 | 4/2005 | Damani et al. | |
| 2005/0126562 A1 | 6/2005 | Rabinowitz et al. | |
| 2005/0131739 A1 | 6/2005 | Rabinowitz et al. | |
| 2005/0268911 A1 | 12/2005 | Cross et al. | |
| 2006/0032496 A1 | 2/2006 | Hale et al. | |
| 2006/0032501 A1 | 2/2006 | Hale et al. | |
| 2006/0120962 A1 | 6/2006 | Rabinowitz et al. | |
| 2006/0153779 A1 | 7/2006 | Rabinowitz et al. | |
| 2006/0177382 A1 | 8/2006 | Rabinowitz et al. | |
| 2006/0193788 A1 | 8/2006 | Hale et al. | |

| | | | |
|---|---|---|---|
| 2006/0216243 A1 | 9/2006 | Rabinowitz et al. | |
| 2006/0216244 A1 | 9/2006 | Rabinowitz et al. | |
| 2006/0233717 A1 | 10/2006 | Hale et al. | |
| 2006/0233718 A1 | 10/2006 | Rabinowitz et al. | |
| 2006/0233719 A1 | 10/2006 | Rabinowitz et al. | |
| 2006/0239936 A1 | 10/2006 | Rabinowitz et al. | |
| 2006/0246011 A1 | 11/2006 | Rabinowitz et al. | |
| 2006/0246012 A1 | 11/2006 | Rabinowitz et al. | |
| 2006/0251587 A1 | 11/2006 | Rabinowitz et al. | |
| 2006/0251588 A1 | 11/2006 | Rabinowitz et al. | |
| 2006/0257328 A1 | 11/2006 | Rabinowitz et al. | |
| 2006/0257329 A1 | 11/2006 | Rabinowitz et al. | |
| 2006/0269486 A1 | 11/2006 | Rabinowitz et al. | |
| 2006/0269487 A1 | 11/2006 | Rabinowitz et al. | |
| 2006/0280692 A1 | 12/2006 | Rabinowitz et al. | |
| 2006/0286042 A1 | 12/2006 | Rabinowitz et al. | |
| 2006/0286043 A1 | 12/2006 | Rabinowitz et al. | |
| 2007/0014737 A1 | 1/2007 | Rabinowitz et al. | |
| 2007/0028916 A1 | 2/2007 | Hale et al. | |
| 2007/0031340 A1 | 2/2007 | Hale et al. | |
| 2007/0122353 A1 | 5/2007 | Hale et al. | |
| 2007/0140982 A1 | 6/2007 | Every et al. | |
| 2007/0178052 A1 | 8/2007 | Rabinowitz et al. | |
| 2007/0286816 A1 | 12/2007 | Hale et al. | |
| 2008/0110872 A1 | 5/2008 | Hale et al. | |

FOREIGN PATENT DOCUMENTS

| | | |
|---|---|---|
| WO | WO 96/13292 | 5/1996 |
| WO | WO 96/30068 | 10/1996 |
| WO | WO 97/27804 | 8/1997 |
| WO | WO 97/35562 | 10/1997 |
| WO | WO 97/35582 | 10/1997 |
| WO | WO 97/36574 | 10/1997 |
| WO | WO 98/22170 | 5/1998 |
| WO | WO 98/31346 | 7/1998 |
| WO | WO 98/36651 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/27359 | 5/2000 |
| WO | WO 00/27363 | 5/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 01/13957 | 3/2001 |
| WO | WO 01/41732 | 6/2001 |
| WO | WO 01/95903 | 12/2001 |
| WO | WO 02/24158 | 3/2002 |
| WO | WO 02/060870 | 8/2002 |
| WO | WO 02/083119 | 10/2002 |
| WO | WO 02/094236 | 11/2002 |
| WO | WO 02/098496 | 12/2002 |
| WO | WO 02/102297 | 12/2002 |
| WO | WO 03/024456 | 3/2003 |
| WO | WO 03/037412 | 5/2003 |

OTHER PUBLICATIONS

Schreiber et al. (1999) "The Atypical Neuroleptics Clozapine and Olanzapine Differ Regarding Their Antinociceptive Mechanisms and Potency" *Pharmacology Biochemistry and Behavior* vol. 64 No. 1: 75-80.
Hamon, et al. (1987) "Opioid Receptors and Neuropeptides in the CNS in Rats Treated Chronically with Amoxapine and Amitriptyline" *Neuropharmacology* vol. 26 No. 6: 531-539.
Pfeiffer, Ronald (1982) "Drugs for pain in the elderly" *Geriatrics* vol. 37 No. 2: 67-76.
Gleeson, et al. (1982) "Chlorpromazine Hyperalgesia Antagonizes Clonidine Analgesia, but Enhances Morphine Analgesia in Rats Tested in a Hot-Water Tail-Flick Paradigm" *Psychopharmacology* vol. 78:141-146.
Lynch, Mary E. (2001) "Antidepressants as analgesics: a review of randomized controlled trials" *J. Psychiatry Neuroscience* vol. 26: 30-36.
Rapoport et al. (1997) CNS Drugs 7(1):37-46.
Bennett, R. L. et al. (1981). "Patient-Controlled Analgesia: A New Concept of Postoperative Pain Relief," Annual Surg. 195(6):700-705.
Bigal, et al. (2002) "Intravenous Chlorpromazine in the Emergency Department Treatment of Migraines: A Randomized Controlled Trial." *The Journal of Emergency Medicine* vol. 23, No. 2: 141-148.
Blanda et al. (2001) "Intranasal Lidocaine for the Treatment of Migraine Headache: A Randomized, Controlled Trial" *Academic Emergency Medicine* vol. 8:337-342.
Bowden, et al. (1988) "The Effect of Trifluoperazine on Bronchial Responsiveness in Asthma" *Clinical and Experimental Pharmacology & Physiology* 15: 457-463.
Caley, C.F. et al. (1998) "Focus on quetiapine: the fourth atypical antipsycotic" Formulary col. 33 No. 2: 105-119.
Carroll, M.E. et al. (1990), "Cocaine-Base Smoking in Rhesus Monkey: Reinforcing and Physiological Effects," Psychopharmacology (Berl) 102:443-450.
Caviness, Verne S. (May, 1980) "Cluster Headache: Response to Chlorpromazine" *Headache* 128-131.
Clark, A. and Byron, P. (1986). "Dependence of Pulmonary Absorption Kinetics on Aerosol Particle Size," Z. Erkrank. 166:13-24.
Collins, et al. (2001) "Intravenous Administration of Prochlorperazine by 15-Minute Infusion Versus 2-Minute Bolus Does Not Affect the Incidence of Akathisia: A prospective Randomized, Controlled Trial" *Annals of Emergency Medicine* 38:5 491-496.
Coppola et al. (1995) Abstract: "A Prospective, Double-blind Evaluation of Prochlorperazine vs. Sumatriptan for the Emergency Department Treatment of Migraine Headache." *Annual Meeting Abstracts* vol. 2 No. 5: 367-368.
Coppola et al. (1995) "Randomized, Placebo-Controlled Evaluation of Prochlorperazine Versus Metoclopramide for Emergency Department Treatment of Migraine Headache" *Annals of Emergency Medicine* vol. 25 No. 5.
Dahloef, et al. (1998) "Pathophysiology and pharmacology of migraine. Is there a place for antiemetics in future treatment stratejies" *Cephalagia* vol. 18: 594-604.
Darquenne, C. et al. (1997). "Aerosol Dispersion in Human Lung: Comparison Between Numerical Simulations and Experiments for Bolus Tests," American Physiological Society. 966-974.
Davies, C. N. et al. (May 1972). "Breathing of Half-Micron Aerosols," Journal of Applied Physiology. 32(5):591-600.
Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.
Donohue et al. (1995) Abstract: "Prochlorperazine Versus Sumatriptan for Emergency Department Therapy of Migraine Headache" *Annals of Emergency Medicine* vol. 25 No. 1: 154.
Drotts, et al. (1999) Ann. Emerg. Med. 34: 469-475.
Finlay, W. H. (2001). "The Mechanics of Inhaled Pharmaceutical Aerosols", Academic Press: San Diego Formula 2.39. pp. 3-14 (Table of Contents). pp. v-viii.
Galeotti Nicoletta et al. (2002). "Indomethacin caffeine and prochlorperazine alone and combined revert hyperalgesia in in vivo models of migraine", Pharmacological research, vol. 46. No. 3: 245-250.
Ginder et al. (2000) "A Prospective Study of I.V. Magnesium and I.V. Prochlorperazine in the Treatment of Headaches" *The Journal of Emergency Medicine*: vol. 18 No. 3: 311-315.
Gonda, I. (1991). "Particle Deposition in the Human Respiratory Tract,"Chapter 176, The Lung: Scientific Foundations. Crystal R.G. and West, J.B. (eds.), Raven Publishers, New York. pp. 2289-2294.
Hansh et al. (1990) Comprehensive medicinal chemistry 5:251-278, Pharmacogenetics.
Hatsukami D., et al. (May 1990) "A Method for Delivery of Precise Doses of Smoked Cocaine-Base to Human." Pharmacology Biochemistry & Behavior. 36(1):1-7.
Jones et al. (1996) "Intramuscular Prochlorperazine Versus Metoclopramide as Single-Agent Therapy for the Treatment of Acute Migraine Headache" *American Journal of Emergency Medicine* vol. 14 No. 3. pp. 262-264.
Kabbouche et al. (2001) "Tolerability and Effectiveness of Prochlorperazine for Intractable Migraine in Children" *Pediatrics* vol. 107 No. 4.

Kelly, Anne-Maree (2000) "Migraine: Pharmacotherapy in the Emergency Department" *WJM* vol. 173: 189-193.

Lane et al. (1989) "Comparative Efficacy of Chlorpromazine and Meperidine with Dimenhydrinate in Migraine Headache."vol. 18:4.

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Lu et al. (2000) "Repetitive Intravenous Prochlorperazine Treatment of Patients with Refractory Chronic Daily Headache." *Headache* vol. 40:724-729.

Martin, B. R. and Lue, L. P. (May/Jun. 1989). "Pyrolysis and Volatilization of Cocaine," Journal of Analytical Toxicology 13:158-162.

Mascia et al. (1998) "Dopamine and migraine: a review of pharmacological, biochemical, neurophysiological, and therapeutic data" *Cephalagia* vol. 18:174-182.

Mattox, A.J. and Carroll, M.E. (1996). "Smoked Heroin Self-Administration in *Rhesus* Monkeys," Psychopharmacology 125:195-201.

Meng, Y. et al. (1997). "Inhalation Studies with Drugs of Abuse", NIDA Research Monogragh 173:201-224.

Meng, Y., et al. (1999). "Pharmacological effects of methamphetamine and other stimulants via inhalation exposure," Drug and Alcohol Dependence. 53:111-120.

Miller-Gibson et al. (2002) "273 Intravenous sodium valproate versus prochlorperazine for the emergency department treatment of acute migraine headache." *Annals of Emergency Medicine* vol. 40 No. 4.

Miner et al. (2001) "Droperidol vs. Prochlorperazine for Benign Headaches in the Emergency Department." *Academic Emergency Medicine* vol. 8 No. 9.

Mineshita et al. (1970) Applied Pharmacology 4:293-303, "T. Toxicity Tests of 2-Chloro-11-(4-methyl-l-piperazinyl)-dibenzo [b,f] [1,4] oxazepine (S 805) (I) Acute, Subacute and Chronic Toxicity of S-805" Oyo Yakuri Pharmacometrics.

Pankow, J. (Mar. 2000). ACS Conference-San Francisco-Mar. 26, 2000. Chemistry of Tobacco Smoke. pp. 1-8.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Peroutka, Stephen J. (1997) "Dopamine and migraine" *Neurology* 49:650-656.

Raskin, N. H. (1994) "Headache" Western Journal of Medicine vol. 161 No. 3:299-302.

Rozen et al. (2001) "Olanzapinea as an Abortive Agent for Cluster Headache." *Headache* vol. 41:813-816.

Saada, Hanna A. (1992) "Abortive Headache Therapy in the Office with Intravenous Dihydroergotamine Plus Prochlorperazine." *Headache* 32:143-146.

Saada, Hanna A. (1994) "Abortive Migraine Therapy in the Office with Dexamethasone and Prochlorperazine." *Headache* 34:366-370.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Seim, et al. (1998) "Intravenous Ketorolac vs. Intravenous Prochlorperazine for the Treatment of Migraine Headaches" *Academic Emergency Medicine* vol. 5, No. 6.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

Sharma, et al. (2002) "Efficacy and Tolerability of Prochlorperazine Buccal Tablets in Treatment of Acute Migraine" *Headache*: 42: 896-932.

Shrestha et al. (1996) "Ketorolac vs Chlorpormazine in the Treatment of Acute Migraine Without Aura." *Arch. Intern. Med.* vol. 156:1725-1728.

Silberstein et al. (2002) "Olanzapine in the Treatment of Refractory Migraine and Chronic Daily Headache" *Headache* vol. 42:515-518.

Tanen et al. (2003) "Intravenous Sodium Valproate Versus Prochlorperazine for the Emergency Department Treatment of Acute Migraine Headaches: A Prospective, Randomized, Double-Blind Trial" *Annals of Emergency Medicine* vol. 41:847-853.

Thomas, et al. (1994) "Intravenous Versus Rectal Prochlorperazine in the Treatment of Benign Vascular or Tension Headache: A Randomized, Prospective, Double-Blind Trial" *Annals of Emergency Medicine* 24:5 923-927.

Vapotronics, Inc. (1998) located at www.vapotronics.com.au/banner. htm., 11 pages, (visited on Jun. 5, 2000).

Wang, Shuu-Jiun et al. (1997) "Droperidol treatment of status migrainosus and refractory migraine" Headache vol. 37 No. 6:376-382.

Ward, M. E. MD, et al. (Dec. 1997). "Morphine Pharmacokinetics after Pulmonary Administration from a Novel Aerosol Delivery System," Clinical Pharmacology & Therapeutics 62(6):596-609.

Wilknson M. (1985). "Migrain-treatment of acute attack", Scottish Medical Journal vol. 30 No. 4: 258-262.

Wood, R.W. et al. (1996). "Methylecgonidine Coats the Crack Particle." Pharmacology Biochemistry & Behavior. 53(1):57-66.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

U.S. Appl. No. 11/687,466, filed Mar. 16, 2007, Zaffaroni et al.
U.S. Appl. No. 11/964,630, filed Dec. 26, 2007, Hale et al.
U.S. Appl. No. 12/045,674, filed Mar. 10, 2008 Wensley.
U.S. Appl. No. 12/111,188, filed Apr. 28, 2008 Hale et al.
U.S. Appl. No. 12/117,737, filed May 8, 2008 Hale et al.
U.S. Appl. No. 12/057,330, filed Mar. 27, 2008 Rabinowitz et al.

www.ashp.org/mngrphs/essentials/a382311e.htm as visited on Feb. 17, 2009.

www.medscape.com/druginfo/monograph?cid=med &drugid=14375&drugname=Loxapine+Succinate+Oral &monotype=monograph&secid=3) as visited on Feb. 17, 2009.

www.medscape.com/druginfo/monograph?cid=med &drugid=14375&drugname=Loxagine+Succinate+Oral &monotype=monograph&secid=8) as visited on Feb. 17, 2009.

Tanaka at al. "New Pharmacology (revised $3^{rd}$ ed.)", 1997, p. 353-354—in Japanese.

Tanaka et al. "New Pharmacology (revised $31^{rd}$ ed. )", 1997, p. 353-354—English translation.

* cited by examiner

METHOD FOR TREATING HEADACHE WITH LOXAPINE

CROSS-REFERENCES TO RELATED APPLICATIONS

This application is related to and claims priority of U.S. Provisional patent application Serial No. 60/429,405, filed Nov. 26, 2002, the entire contents of which are hereby incorporated herein.

BACKGROUND OF THE INVENTION

This invention relates to treatment and control of pain by administering to a subject in need of such treatment or control an effective amount of loxapine or amoxapine, or of a substance that provides loxapine or amoxapine in the body. More particularly this invention relates to treatment or control of pain by systematically administering, for example by inhalation, loxapine, amoxapine, or a substance that provides loxapine or amoxapine in the body.

Loxapine [2-chloro-11(4-methyl-1-piperazinyl)dibenz(b, f) (1,4) oxazepine] is an antipsychotic drug particularly useful for treating schizophrenia or related psychotic conditions. It is commercially available in the form of a salt, typically the hydrochloride or succinate. Amoxapine [2-chloro-11(1-piperazinyl)dibenz(b,f) (1,4) oxazepine] is a known antidepressant that differs from other antidepressants in that it has both antidepressant and antipsychotic efficacy. Thus, amoxapine, unlike other antidepressants, is used mainly in treatment of psychotic depression.

Some patents and literature indicate that selected antipsychotics and/or antidepressant drugs may treat pain to a certain degree. However, data supporting these suppositions have been scattered and spotty, with some drugs showing some capability for controlling pain to varying degrees; whereas, other compounds from the same pharmacological class are completely ineffective in pain control. Thus, no real overall pattern emerges.

For example, U.S. Pat. Nos. 5,929,070, 5,945,416, and 6,258,807 disclose the use of olanzapine, alone or in combinations, to treat various types of pain. U.S. Pat. No. 6,444,665 discloses the use of several a typical antipsychotic compounds, namely risperidone, clozapine, quetiapine, sertindole, ziprasidone and zotepine, in treatment of pain especially when administered with a number of other pain-relieving drugs. On the other hand, another study [Schreiber et al., (1999) Pharmacology Biochemistry Behavior 64:75], documents that there are differences between a typical antipsychotics, even from the same class (e.g., olanzapine and clozapine), in their ability to control pain; and thereby demonstrates that analgesic effects are not a common class effect of antipsychotic medications.

U.S. Pat. No. 6,290,986 discloses transdermal administration of various drugs to control localized pain, in a special formulation comprising a lecithin organogel. Some antidepressant drugs are disclosed for use in such formulations, notably amitriptyline and doxepin. Those antidepressants are, however, claimed to be effective only in combination with guaifenesin, a compound known to have analgesic effects on its own, and there is no indication on the efficacy of the antidepressants when administered without guaifenesin. At the end of the patent text a "belief" is expressed that a number of other tricyclic drugs including amoxapine will show similar activity. In a later patent in the same series, U.S. Pat. No. 6,479,074, amoxapine is included in a list of tricyclic compounds that are said to be useful in some transdermal compositions for treating localized pain, again given in combination with guaifenesin. However, no data are reported for amoxapine. Similarly, U.S. Pat. No. 6,638,981 asserts that compositions containing antidepressants are effective in treating localized pain using topically applied compositions due to their local anesthetic effects. Analgesic effects of antidepressants after systemic administration, are, however, not suggested in that patent. Ten categories of antidepressants are mentioned, including a miscellaneous or "catch all" category. Each category includes a lengthy list of compounds supposedly having activity against pain. Amoxapine is listed among a number of other compounds in one of these categories but again no data are presented for it, or indeed for most of the compounds individually named in the patent. To the contrary, the data focus on two compounds—amitriptyline and ketamine. U.S. Pat. Nos. 5,900,249 and 6,211,171 also mention amoxapine in a list of compounds said to be useful in controlling pain when incorporated in topical compositions (e.g. as local anesthetics) but, yet again, no data are presented for amoxapine and no analgesic efficacy of antidepressants after systemic administration is suggested.

Lynch, ["Antidepressants as analgesics: a review of randomized controlled trials" (2001) Revue de Psychiatre et de Neuroscience 26:30], summarized the results of 59 randomized placebo-controlled trials examining the analgesic effect of antidepressants thus: "There is significant evidence that the tricyclic group of antidepressants is analgesic and that trazodone is not; the data regarding selective serotonin reuptake inhibitors are conflicting." However, even in the case of tricyclic antidepressants, the list of 41 references involved work with only five such compounds (amitriptyline, doxepin, imipramine, clomipramine and desipramine) and did not include any reports for either loxapine or amoxapine, which differ significantly from the compounds tested in their mechanism of action.

In brief, a few antidepressants have been shown to have some analgesic properties, primarily when applied as topical or transdermal compositions, to control local pain or to provide local anesthesia. However, the effectiveness of these compounds is not related to their antidepressant activity and is not shown as representing any type of a class effect. Moreover, while another study [Hamon et al., (1987) Neuropharmacology 26: 531-539] showed that analgesic effects of morphine were enhanced after chronic treatment with amoxapine in an animal model, the results indicated that amoxapine itself had no effect on pain. FIG. 1 of that reference shows that there was no change in the latency of the tail-flick after chronic administration of amoxapine alone, thus indicating that amoxapine alone had essentially no effect on pain. In another reference, Pfeiffer [(1982) Geriatrics 27:67] states that some tricyclic antidepressants, including amoxapine, are "given with good results to patients who manifest pain as a somatization of depression". Again, this is distinguishable in that these antidepressants are used to treat a somatization of depression that is manifested as pain, and not actual pain.

In short, amoxapine has been listed (in some of the above-mentioned patents) among a number of compounds that are believed to have some such activity, but no data are presented confirming that it has this capability, and one study showed a lack of such activity. Additionally, in contrast to references suggesting that the use of antipsychotics may reduce pain, some antipsychotics have been actually shown to produce the opposite effect, an increase in pain [see Frussa-Filho et al., (1996) Arch Int Pharmacodyn 331: 74-93 (haloperidol) and Gleeson et al. (1982). Psychopharmacology 78: 141-146 (chlorpromazine)]. Capability, if any, of amoxapine in controlling pain, particularly pain that is not localized, cannot be ascertained from this paucity of information, and there is no information in the art on whether loxapine would have any pain-controlling effect of any nature.

BRIEF SUMMARY OF THE INVENTION

This invention comprises treating or controlling pain, by administering an effective amount of loxapine or amoxapine systemically or to the brain. Preferably the loxapine or amoxapine is administered by inhalation. The invention also comprises methods of administering loxapine or amoxapine for treatment of pain, as above, and formulations for so administering them.

DETAILED DESCRIPTION OF THE INVENTION

Figure 1:
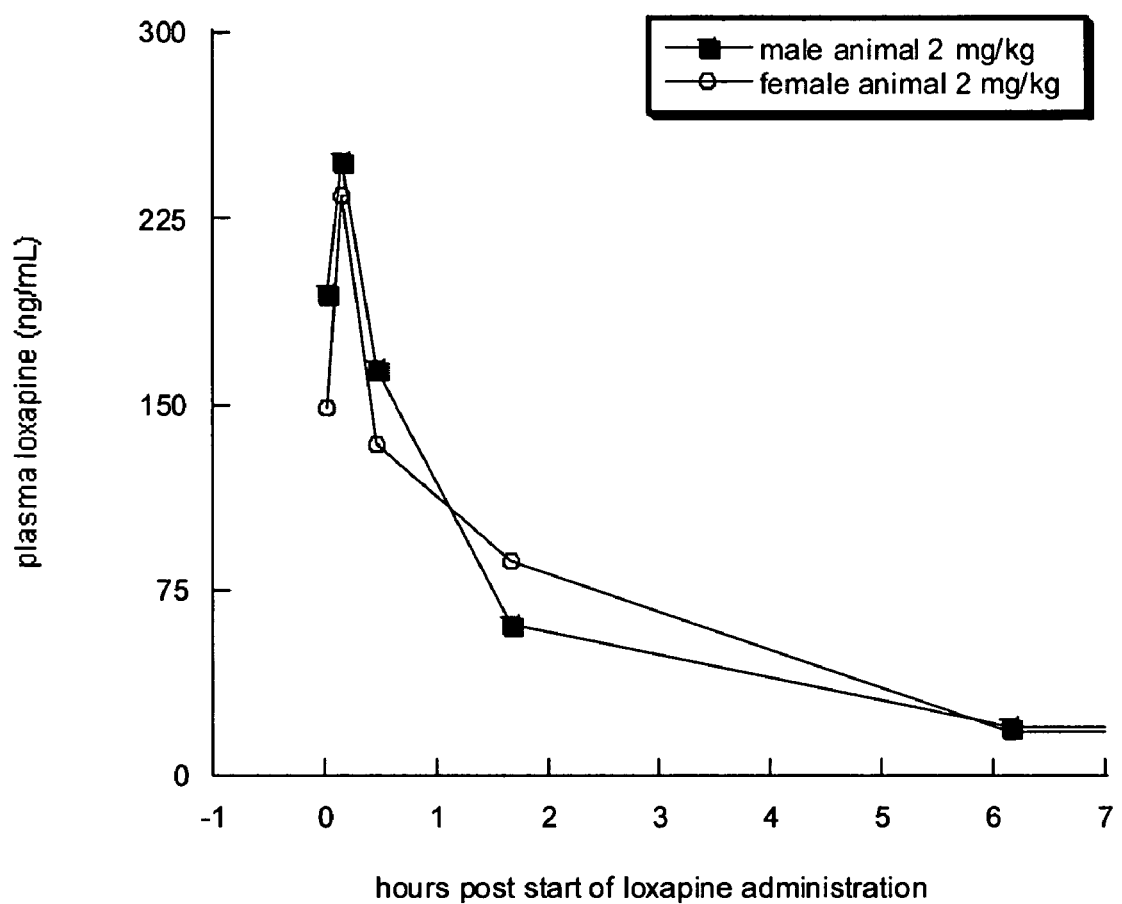
FIG. 1 is a plot showing plasma concentration (ng/mL) of loxapine hours post start of loxapine administration via inhalation at a dose of 2 mg/kg in beagle dogs.

Loxapine [2-chloro-11(4-methyl-1-piperazinyl)dibenz(b, f) (1,4) oxazepine] is an antipsychotic drug particularly useful for treating schizophrenia or related psychotic conditions. It is commercially available in the form of a salt, typically the hydrochloride or succinate. Amoxapine [2-chloro-11(1-piperazinyl)dibenz(b,f) (1,4) oxazepine] is a known antidepressant with antipsychotic properties.

Neither loxapine nor amoxapine has previously been shown to be effective in treatment or control of pain. We have found, however, that these substances are surprisingly effective in treating or controlling pain, especially headache pain, including migraine, tension headache and cluster headache.

The treatment or control of pain according to this invention is accomplished by administering to a patient or subject in need of such treatment, an effective pain-relieving or -alleviating amount of amoxapine, loxapine, pharmaceutically acceptable salts of either of them, or prodrugs of either of them. The use of salts or prodrugs of the active ingredient can provide effective means for providing the appropriate amount of loxapine or amoxapine, respectively, to the subject, and may provide advantages in formulating, packaging, or otherwise preparing and/or administering the active ingredients.

In one aspect of this invention, an effective pain-alleviating amount of loxapine or amoxapine, or a pharmaceutically acceptable salt or prodrug of loxapine or amoxapine, is administered to treat a patient or subject. By "effective pain-alleviating amount" is meant an amount of the substance in question that suppresses or inhibits pain. This invention is applicable to both the alleviation of existing pain as well as to the suppression or inhibition of pain that would be expected to ensue from an imminent pain-causing event.

The terms "alleviating," "suppressing," and "inhibiting" refer to indicia of success in the treatment or alleviating of pain, including both objective and subjective parameters such as abatement, diminishing of symptoms, making the pain symptom or condition more tolerable to the patient or subject, decreasing duration of the pain or decreasing the onset of pain expected to occur after an event. When referring to treatment of headache, including migraine headache, the terms "alleviating," "suppressing," and "inhibiting" refer to indicia of success in the treatment or alleviating of any existing headache or any aura of a headache, including both objective and subjective parameters such as abatement, diminishing of symptoms, making the headache more tolerable to the patient or subject, decreasing the duration of the headache or decreasing headache pain anticipated to follow the headache aura and specifically excludes decreasing the frequency of the pain (headache) or preventing the occurrence of the pain (headache), except when such decrease in frequency or such prevention of occurrence is achieved by use of the medication specifically during a headache aura or at the first sign of the headache itself; thus, when referring to the treatment of headache the terms "alleviating," "suppressing," and "inhibiting" specifically exclude chronic use of the medication for the purposes of headache prevention.

As used herein, "pain" includes all types of pain. More specific types of pain encompassed by this term include neuropathic pain, inflammatory pain, nociceptive pain, acute pain, chronic pain, regional pain, generalized pain, post-operative pain, dental pain, migraine, cluster headaches, tension headaches, neuralgia, cancer pain, resistant pain, pain resulting from burns, labor and delivery pain, postpartum pain, irritable bowel syndrome, fibromyalgia, pancreatic pain, myocardial infarction pain, and temporal-mandibulla disorders. Of particular relevance in this invention is the treatment of migraine, cluster headaches and tension headaches, and of other types of pain, by accessing the central nervous system, especially by systemic administration of an effective amount of loxapine or amoxapine, or a salt or prodrug of either.

The terms "subject" or "patient" refer to a vertebrate animal, preferably mammals including primate mammals such as humans and other mammals, including non-primate mammals such as pets, domestic animals, and the like.

The term "pharmaceutically acceptable salts" is meant to include salts of the active compounds which are prepared with relatively nontoxic acids, depending on the particular substituents found on the compounds described herein. By "pharmaceutically acceptable" is meant that the salt in question is or can be approved by a regulatory agency of the Federal, state, or other foreign government or listed in the U.S. Pharmacopoeia or other generally recognized pharmacopeias for use in animals, more particularly in humans. Since compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen-carbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al., "Pharmaceutical Salts", *Journal of Pharmaceutical Science,* 1977, 66, 1-19).

Starting from the salts, the neutral forms of the compounds may be regenerated by contacting the salt with a base [or acid] and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides active compounds in a prodrug form. Prodrugs of the compounds described herein are those compounds that readily undergo chemical changes under chemical, biochemical or physiological conditions to provide loxapine or amoxapine, respectively. For example, prodrugs of loxapine or amoxapine include compounds that can be hydrolyzed, oxidized, hydrogenated, cleaved or otherwise reacted under biological conditions, in vitro or in vivo, to produce the active compound. Some phosphonooxymethyl prodrugs of loxapine are disclosed in Krise et al., J Pharm Sci. (1999) 88:922 and 928 and J Med Chem. (1999) 42:3094.

When used to treat a subject for alleviation of pain, particularly for treatment of migraine, loxapine or amoxapine will be employed in dosages generally below those used for their current purposes of treating schizophrenia and depression, respectively.

As described in the Physicians' Desk Reference (57th edition, 2003), recommended initial oral administration of loxapine in treatment of schizophrenia is 10-20 mg/day administered in 2-4 doses. This dose is, however, generally not effective and is titrated up with common oral dose being in the 20-100 mg/day range, typically in the 60-100 mg range and up to 250 mg. A typical single acute dose is 20-50 mg. The typical intramuscular daily dose of loxapine is 50-150 mg for treatment of severe mental disturbances (mainly schizophrenia)—the total dose is usually divided into 2-4 doses as with oral administration. Based on studies conducted by the manufacturer of loxapine-containing products [Lederle Laboratories] the $T_{max}$ after oral administration is 2-3 hrs. Information on the $C_{max}$ after oral administration is controversial with conflicting reports from two studies. According to one study, $C_{max}$ for loxapine and its metabolites is ~0.35 µg/ml after oral dose of 25 mg. However, according to a different study, $C_{max}$ for loxapine only is ~10-12 ng/ml after oral dose of 25 mg. There is no definitive PK study with intramuscular formulation. However, behavioral observations would indicate that the absorption is relatively slow.

For treatment of migraine headache according to this invention, however, loxapine is administered at a dosage of from about 0.3 to about 20 mg per single dose, preferably from about 1 to about 10 mg, most preferably from about 2 to about 6 mg. Generally, a single dose at the time of the migraine attack is effective, with no need to take multiple doses per day. In certain embodiments of the invention, the above doses are given as a series of smaller doses until migraine relief is achieved.

Typical oral daily doses of amoxapine in treatment of depression are 200-400 mg. Treatment is typically started with the oral dose of 50 mg administered 3 times per day (i.e. the total daily dose is 150 mg) and the dose is gradually titrated up. The $T_{max}$ for amoxapine after oral administration is ~1.5 hrs after oral administration of 100 mg. The $C_{max}$ after the same dose is ~50 ng/ml [Calvo et al., Int J Clin Pharmacol Ther Toxicol (1985) 23:180]. After the lowest used oral dose (50 mg), the $C_{max}$ is ~30 ng/ml [Jue et al., Drugs (1982) 24:1). After repeated amoxapine dosing, there is accumulation of active drug—the blood levels are in ~30-300 ng/ml range (Calvo et al. 1985).

For treatment of migraine headache according to this invention, however, amoxapine is administered at a dosage from about 3 to about 100 mg per single dose, preferably from about 10 to about 40 mg.

Loxapine- or amoxapine-containing compositions may be administered to the patient or subject in any of a variety of ways that enable systemic administration. These include administration by inhalation, parenteral administration, e.g. by injection (e.g., intradermal, intramuscular, intra- peritoneal, intravenous, intrathecal or subcutaneous) and mucosal (e.g., intranasal, oral, or rectal routes). In preferred embodiments of the present invention, pharmaceutical compositions containing loxapine or amoxapine are administered by inhalation or injection, or mucosally, including, but not limited to nasal, sublingual (or other oral cavity administration), pulmonary (i.e., inhaled into the lungs, such as by an inhaler or nebulizer), and rectal administration. The active ingredient thereof may be administered alone or together with other biologically active agents, e.g., as described in this section. Administration can be systemic or local, but is preferably systemic. If local, administration is preferably via the nose directly to the brain, without drug first entering the systemic circulation. Such entry of drug to the brain via the nose may occur by drug passing through extracellular spaces in the olfactory tract.

The pharmaceutical compositions of the invention are formulated to be compatible with the intended route of administration, as described above. As is known in the art, different types of compositions are typically prepared for use in different routes of administration. In general, compositions will contain various excipients, additives, and agents included for purposes such as storage stability, ease of administration, and the like.

For instance, compositions for intravenous administration or other injections typically are solutions in sterile isotonic aqueous buffer. Where necessary, the composition may also include a solubilizing agent and a local anesthetic such as lidocaine to ease pain at the site of the injection.

If the compositions of the invention are to be administered orally, they can be formulated in the form of, e.g., tablets, capsules, cachets, gelcaps, solutions, suspensions and the like. Tablets or capsules can be prepared by conventional means with pharmaceutically acceptable excipients such as binding agents (e.g., pregelatinized cornstarch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well-known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated for slow release, controlled release or sustained release of prophylactic or therapeutic agent(s).

The compositions of the invention may also be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

If the compositions of the invention are to be administered mucosally through the nasal cavity, the compositions can be formulated in an aerosol form, spray, mist or in the form of drops. In particular, the compositions of the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compositions of the invention may also be formulated in rectal compositions such as suppositories or retention enemas, e.g., containing conventional suppository bases such as cocoa butter or other glycerides.

The compositions of the invention may also be formulated for transdermal administration. For transdermal administration, the active compounds are formulated into ointments, salves, gels, or creams as generally known in the art. Pharmaceutical compositions adapted for transdermal administration can be provided as discrete patches intended to remain in intimate contact with the epidermis for a prolonged period of time. If the compositions of the invention are to be administered topically, the compositions can be formulated in the form of, e.g., an ointment, cream, transdermal patch, lotion, gel, spray, aerosol, solution, emulsion, or other form well-known to one of skill in the art. For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as Freon), or in a squeeze bottle. Moisturizers or humectants can also be added to pharmaceutical compositions and dosage forms if desired. Examples of such additional ingredients are well-known in the art.

The compositions of the invention may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

In a specific embodiment, the pharmaceutical composition can be delivered in a controlled or sustained release system. In one embodiment, a pump may be used to achieve a controlled or sustained release (see Langer, Science, 249:1527-1533 (1990); Sefton, 1987, CRC Crit. Ref. Biomed. Eng. 14:10; Buschwald et al., 1980, Surgery 88:507; Saudek et al., 1989 N. Engl. J. Med. 321:574). In another embodiment, polymeric materials can be used to achieve controlled or sustained release of the active ingredient (see e.g., Medical Applications of Controlled Release, Langer and Wise (eds.), CRC Pres., Boca Raton, Fla. 1974); Controlled Drug Bioavailability, Drug Product Design and Performance, Smolen and Ball (eds.), Wiley, New York (1984); Ranger and Peppas, 1983, J. Macromol. Sci. Rev. Macrol. Chem. 23:61; see also Levy et al., 1985 Science 228:190; During et al., 1989, Ann. Neurol. 25:35 1; Howard et al., 1989, J. Neurosurg. 71:105; U.S. Pat. Nos. 5,679,377; 5,916,597, 5,912,015; 5,989,463; 5,128,326; PCT Publication No. WO 99/12154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polyactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity to the therapeutic target, thus requiring only a fraction of the systematic dose (see, e.g., Goodson, in Medical Applications of Controlled Release, supra, vol. 2, pp. 115-138 (1984)).

A preferred method of administration of loxapine and amoxapine, as a feature of the invention, is administration by inhalation, or pulmonary administration. Pulmonary drug delivery can be achieved by several different approaches, including liquid nebulizers, aerosol-based metered dose inhalers (MDI's), and dry powder dispersion devices. Compositions for use in administrations of this type are typically dry powders or aerosols. For administration of aerosols, which is the preferred method of administration of this invention, the compositions are generally delivered by inhalers, some types of which are described below.

Dry powders contain, in addition to the active ingredient, a carrier, an absorption enhancer, and optionally other ingredients. The carrier is, for example, a mono-, di- or polysaccharide, a sugar alcohol or another polyol. Suitable carriers include lactose, glucose, raffinose, melezitose, lactitol, maltitol, trehalose, sucrose, mannitol; and starch. Lactose is particularly preferred, especially in the form of its monohydrate. Also included are absorption enhancers such as polypeptides, surfactants, alkyl glycosides, amine salts of fatty acids or phospholipids. The ingredients of the formulation typically must be in a finely divided form, i.e. their mass median diameter should generally be less than about 5-10 μm, preferably from about 1 to about 5 μm, as measured by a laser diffraction instrument or a Coulter counter. The desired particle size may be produced using methods known in the art, e.g. milling, micronization or direct precipitation.

For administration by inhalation the compounds according to the invention are conveniently delivered in the form of a condensation aerosol as discussed in U.S. patent application Ser. No. 10/152,639, filed May 20, 2003, which is hereby incorporated by reference herein, in its entirety. Preferred for use in this invention is inhalation or pulmonary administration of loxapine or amoxapine in the form of an aerosol, preferably one having a mass median aerodynamic diameter (MMAD) of between about 0.01 and about 3 μm. Such aerosols may be produced from a thin film of the drug, which itself may be produced using a solution of the drug in an appropriate solvent or a melt of the drug itself. Particularly suitable devices for producing aerosols of loxapine and amoxapine from such thin films, where the film preferably has a thickness of from abut 0.05 to about 20 μm, are disclosed in pending U.S. patent application Ser. No. 10/633,877 filed Aug. 4, 2003 titled "Thin-Film Drug Delivery Article and Method of Use" and Ser. No. 10/633,876, filed Aug. 4, 2003 titled "Rapid-Heating Drug Delivery Article and Method of Use" both of which are hereby incorporated herein by reference in their entireties. Production of such aerosols is preferably carried out under vaporization conditions sufficient to provide at least 50% recovery of the active ingredient in an aerosol and wherein said aerosol contains less than about 5% by weight of compound degradation products.

When amoxapine and loxapine are used for treating attacks of headache, particularly migraine headache, it is preferred that the amoxapine or loxapine is delivered rapidly such that maximum plasma levels occur within preferably 30 minutes, more preferably 15 minutes, or most preferably 5 minutes of drug administration. Such rapid drug absorption can be achieved by routes including intravenous delivery or aerosol inhalation, but again aerosol administration is the preferred route.

More particularly, for migraine treatment the invention provides a method of delivery of loxapine wherein maximum blood levels of drug are achieved within 30 minutes from administration, preferably within 15 minutes from administration. This can result in a peak rate of increase in blood levels of loxapine of at least 1 ng/ml/minute, and blood levels of at least 5 ng/ml of loxapine within 15 minutes from administration.

For migraine treatment using amoxapine the invention likewise provides a method of delivery of amoxapine wherein maximum blood levels of amoxapine are achieved within 30 minutes from administration, preferably within 15 minutes of administration. This can result in a peak rate of increase of blood levels of amoxapine of at least 3 ng/ml/minute and blood levels of at least 10 ng/ml of amoxapine within 15 minutes of administration.

Rapid achievement of these levels of the drug is preferably accomplished by producing aerosols from thin films of the drugs, most preferably using the thin-film and rapid-heating devices disclosed in the two patent applications mentioned above.

The compositions of the invention can be used in combination therapy with one or more other therapeutic agents, provided the combination administration does not result in inhibition of the pain-alleviating action of the loxapine or amoxapine or produce undesirable combination effects. The loxapine or amoxapine and the other therapeutic agent or agents can act additively or synergistically. In a preferred embodiment, a composition of the invention is administered concurrently with the administration of another therapeutic agent, which can be part of the same composition as, or in a different composition from, that containing the loxapine or amoxapine of the invention. In another embodiment, the loxapine or amoxapine is administered prior or subsequent to administration of another therapeutic agent. In one embodiment of combination therapy that involves treatment of chronic pain, the combination therapy involves alternating between administering a composition comprising loxapine or amoxapine and a composition comprising another therapeutic agent, e.g., to minimize the toxicity associated with a particular drug. The duration of administration of either can be, e.g., one month, three months, six months, a year, or for more extended periods. In certain embodiments, when a compound of the invention is administered concurrently with another therapeutic agent that potentially produces adverse side effects including, but not limited to, toxicity, the therapeutic agent can advantageously be administered at a dose that falls below the threshold at which the adverse side is elicited.

For example, loxapine or amoxapine, in amounts or dosages of the present invention, can be combined in dosage forms with other analgesics, e.g., opioids, non-steroidal anti-inflammatory agents (NSAIDs), etc., including hydromorphone, codeine, morphine, nicomorphine, hydroxycodone, fentanyl, aspirin, ibuprofen, diclofenac, naproxen, benoxaporfen, flurbiprofen, fenoprofen, ketoprofen, indoprofen, carporfen, oxaprozin, suprofen, tiaprofenic acid, indomethacin, sulindac, tolmetin, zomepirac, acemetacin, fentiaza, mefenamic acid, meclofenamic acid, flufenamic acid, niflumic acid, tolfenamic acid, piroxicam, isoxicam, or pharmaceutically acceptable salts, prodrugs, or mixtures thereof. Other suitable analgesics that may be included in dosage forms of the present invention include steroidal anti-inflammatory drugs, for instance, glucocorticoids, dexamethasone (DECADRON™), cortisone, hydrocortisone, prednisone, prednisolone, triamcinolone; eicosanoids, such as prostaglandins, thromboxanes, and leukotrienes; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; cyclooxygenaze 2 specific inhibitors, including celecoxib, rofecoxib, valdecoxib, eterocoxib and parecoxib; heteroaryl acetic acids, including tolmetin, and ketorolac; anthtanilic acids, including mefanamic acid, and meclofenamic acid; enolic acids, including oxicams (e.g., piroxicam or tenoxicam), and pyrazolidinediones (e.g., phenylbutazone); and alkanones, including nabumetone.

The loxapine or amoxapine may also be formulated in a pharmaceutical dosage form in combination with other anti-migraine agents, such as alpiropride, dihydroergotamine, dolasetron, ergocornine, ergocorninine, ergocryptine, ergot, ergotamine, fonazine, lisuride, lomerizine, methysergide oxetorone, pizotyline, sumatriptan, rizatriptan, naratriptan, eletriptan, frovatriptan, donitriptan, zolmitriptan and mixtures thereof.

The loxapine or amoxapine may also be formulated in a pharmaceutical dosage form in combination with antidepressants. Suitable antidepressants include, but are not limited to, caroxazone, citalopram, dimethazan, fencamine, indalpine, indeloxazine hydrocholoride, nefopam, nomifensine, oxypertine, paroxetine, sertraline, thiazesim, trazodone, iproclozide, iproniazid, isocarboxazid, octamoxin, phenelzine, cotinine, rolipram, maprotiline, metralindole, mianserin, mirtazepine, adinazolam, amitriptyline, amitriptylinoxide, butriptyline, clomipramine, demexiptiline, desipramine, dibenzepin, dimetacrine, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Similarly loxapine or amoxapine can be combined with antiepileptic drugs, e.g., valproate, phenyloin, phenobarbital, primidone carbamazepine, ethosuximide or clonazepam.

EXAMPLES

The following examples further illustrate the invention described herein and are in no way intended to limit the scope of the invention.

Working Examples

Example 1

Mouse Writhing Test

Male mice weighing 23-28 g were used in this test. Mice were injected with acetic acid (0.5% i.p.). This treatment induces a recognizable writhing response in control animals. The number of writhes is counted for 10 minutes beginning 5 minutes after injection of acetic acid. Ten mice were studied per group. The test was performed blind. Loxapine and amoxapine (dispersed in 0.2% hydroxypropylmethylcellulose, then dissolved in saline) were evaluated at five doses, administered i.p. 30 minutes before acetic acid, and compared with a vehicle control (0.2% hydroxypropylmethylcellulose in saline) group. Dosage rates for loxapine were 0.125, 0.25, 0.5, 1 and 2 mg/kg. Dosage rates for amoxapine were 1, 2, 4, 8 and 16 mg/kg. Morphine (8 mg/kg i.p.) administered under the same experimental conditions, was used as reference substance. The data were analyzed by comparing the treated groups with the vehicle control using Mann Whitney U tests.

The results are shown in Table 1:

TABLE 1

Reduction in acetic acid writhing after pretreatment with amoxapine, loxapine and morphine. Data are expressed as a percentage of control vehicle pretreatment.

| SUBSTANCE | DOSE (mg/kg) i.p. | | | | | | | |
|---|---|---|---|---|---|---|---|---|
| | 0.125 | 0.25 | 0.5 | 1 | 2 | 4 | 8 | 16 |
| AMOXAPINE | | | | | | | | |
| First experiment | | | | | | −71% *** | −93% *** | −100% *** |
| Second experiment | | | | −23% NS | −39% * | −71% *** | | |
| MORPHINE | | | | | | | | |
| First experiment | | | | | | | −98% *** | |
| Second experiment | | | | | | | −95% *** | |
| LOXAPINE | | | | | | | | |
| First experiment | | | −99% *** | −100% *** | −99% *** | | | |
| Second experiment | −57% ** | −90% *** | −77% *** | | | | | |
| MORPHINE | | | | | | | | |
| First experiment | | | | | | | −88% *** | |
| Second experiment | | | | | | | −93% *** | |

Mann-Whitney U test: NS = Not Significant;
* = p <0.05;
** = p <0.01;
*** = p <0.001

As shown in Table 1, amoxapine dose-dependently decreased the number of writhes induced by acetic acid, and significantly so from 2 mg/kg. A clear effect was observed from 4 mg/kg. Loxapine dose-dependently decreased the number of writhes induced by acetic acid, and significantly so from 0.125 mg/kg. A marked effect was observed from 0.25 mg/kg. Sedation was observed from 2 mg/kg for amoxapine and from 0.25 mg/kg for loxapine. Morphine markedly antagonized writhing induced by acetic acid in each experiment.

Example 2

An Acute And 5-Day Repeat Dose Toxicity Study Of Inhaled Aerosol Formulations of Loxapine in the Beagle Dog The purpose of the study was to investigate the individual maximum tolerated doses and the potential toxicity of two clinically relevant doses of loxapine in a 5-day repeat dose study in the dog.

This research was conducted at CTBR, 87 Senneville Road, Senneville, Quebec, Canada, H9X 3R3 in compliance with CTBR's Standard Operating Procedures.

The test article was Loxapine aerosol delivered by oropharyngeal inhalation.

The animals used were beagle dogs purchased from Covance Research Product, Route 2, Box 113, Cumberland, VA 23040 of approximately 7-10 months and 6-12 kg at the onset of treatment. Animals were housed individually in stainless steel cages equipped with a bar-type floor and an automatic watering valve. Each cage was clearly labeled with a color-coded cage card indicating project, group, animal and tattoo number and sex. Each animal was uniquely identified by a permanent tattoo number and/or letter on the ventral aspect of one pinna.

The conditions for animal room environment and photoperiod were as follows:

| | |
|---|---|
| Temperature | 20 ± 3° C. |
| Humidity | 50 ± 20% |
| Light cycle | 12 hours light and 12 hours dark (except during designated procedures) |

All animals had access to a standard certified pelleted commercial dog food (400 g—PMI Certified Dog Chow 5007: PMI Nutrition International Inc.) except during designated procedures.

Maximum allowable concentrations of contaminants in the diet (e.g., heavy metals, aflatoxin, organophosphate, chlorinated hydrocarbons, PCBs) were controlled.

Municipal tap water which had been softened, purified by reverse osmosis and exposed to ultraviolet light was freely available (except during designated procedures).

An acclimation period of approximately 3 weeks was allowed between animal receipt and the start of treatment in order to accustom the animals to the laboratory environment.

Before treatment initiation, all animals were weighed and assigned to treatment groups using a randomization procedure. Randomization was by stratification using body weight as the parameter. Males and females were randomized separately. Final animal allocation was checked to ensure that littermates are homogeneously distributed across all groups.

Animals were assigned into the following groups: repeat dose loxapine 2 mg/kg (2 males and 2 females), repeat dose loxapine 0.2 mg/kg (2 males and 2 females), vehicle control repeat dose (2 males and 2 females), and loxapine single escalating doses separated by at least 48 hours (1 male and 1 female).

Animals were treated with the test aerosols using an oropharyngeal face mask fitted with inlet and outlet tubes. During treatment, animals were placed in a restraint sling.

A mask that allows the inhalation of test material to dogs was used. This mask consisted of a plastic cylinder and was fitted over the dog's muzzle in such a way that the nose was inside the cylinder and the animal was mouth breathing through a short tube. The test article was generated by vaporizing loxapine by heating to roughly 400° C. an approximately 4 micron thick film of loxapine which had been formed on stainless steel foil by dip coating the foil into a solution of loxapine dissolved in organic solvent. The resulting aerosol formed by the condensation of the vaporized loxapine was introduced into a mixing chamber via pre-dried compressed air. The mixing chamber was operated under slight positive pressure maintained by means of a gate valve located in the exhaust line. A vacuum pump was used to exhaust the inhalation chamber at the required flow rate and draw the contaminated air (excess aerosol and expired air) through a purifying system consisting of a 5 μm coarse filter before expelling the air from the building. The resulting atmosphere was carried to the dog mask via a delivery tube.

The vehicle control group was exposed to predried compressed air passed through the drug-heating apparatus with the apparatus loaded with clean stainless steel foil instead of loxapine-coated foil. Except for absence of drug, exposure was matched to the 2 mg/kg repeat dose group, in terms of the air being passed through the operating and thus heating apparatus and the dogs breathing only through the dog masks, and the dogs being restrained and handled in the same manner.

To ensure that the doses were correct, prior to the start of the treatment each day, atmosphere characterization of the test article aerosol was performed. The exposure system's operational conditions required to establish each target aerosol concentration was determined gravimetrically from open-face glass fiber filter samples collected at a representative animal exposure mask.

The homogeneity of chamber atmosphere concentration was also determined at 0.2 mg/kg and 2 mg/kg dose levels for loxapine. This comprised collecting filter samples in duplicate for gravimetric analysis from 2 equidistantly spaced dog breathing ports located about the circumference of the mixing chamber. Additional samples were also collected from a reference port to assess total and within port variation of test article distribution within the chamber. The results obtained from this analysis demonstrated uniform aerosol distribution.

Analysis of the aerosol particle size distribution for each loxapine dose was conducted using a Cascade Impactor. The method consisted of classification into a series of size ranges followed by gravimetric analysis. The mass median diameter and its geometric standard deviation (MMAD±GSD) was calculated from the gravimetric data using a computer program based on the Andersen Operating Manual TR#76-900016. Typical mass median aerodynamic diameter and GSD measured during the study were 1.4 μm±2.2.

Actual mask output concentrations of aerosol were measured at least once during each exposure day from a sampling port from the animal breathing zone using a gravimetric method.

The achieved dose of active ingredient (mg/kg/day) for each treatment level was determined as follows:

$$\text{Achieved Dose of active Ingredient (mg/kg/day)} = \frac{RMV \times \text{Active Concentration} \times T \times D}{BW}$$

Where RMV (L/min) = respiratory minute volume*
Active Concentration (mg/L) = chamber concentration of active ingredient determined by chemical analysis.
T (min) = treatment time
D = total aerosol deposition fraction, according to the particle size
BW (kg) = mean body weight per sex per group from the regular body weight occasions during treatment.

Measured using the Buxco Electronics LS-20 system for each animal twice prior to first drug treatment.

An exemplary calculation of the achieved dose of active ingredient, taken from a particular dosing day of the escalating dose portion of the study is as follows:

Mean chamber aerosol concentration: 0.489 mg/L

MMAD±GSD: 1.1 μm±2.2. Based on Witschi & Nettesheim, Mechanisms in Respiratory Toxicology, Vol. 1:54-56, CRC Press, Inc. 1982, the above MMAD and GSD result in a deposition fraction (D) of 0.38.

Mean BW: 8.3 kg

Mean pre-study RMV: 7.86 L/min (assumed not to change during the study)

Exposure time: 15 minutes

Applying the formula as in the above table the above data yield an achieved dose of 2.6 mg/kg.

Dogs were treated with the loxapine aerosol using the above approach to deliver the drug aerosol and compute the delivered dose. Initially, 1 male and 1 female received loxapine 1 mg/kg/dose which resulted in no observable changes in animal behavior. Several days later, these same animals received loxapine 2.6 mg/kg, which resulted in weakness, tremors, and decreased activity.

Subsequently, 2 male and 2 female dogs received vehicle control as described above for 5 days. They showed no behavioral changes. Additionally, 2 male and 2 female dogs received loxapine 0.2 mg/kg (daily) for 5 days. They showed no behavioral changes. Finally, 2 male and 2 female dogs received loxapine 2 mg/kg (daily) for 5 days. They showed weakness, tremors, and decreased activity, but no respiratory adverse findings such as cough. Notably, no signs of bronchoconstriction such as wheezing, prolonged expiratory phase, or cough were found. Food consumption was roughly normal in all animals.

Animals were necropsied on completion of the treatment period by exsanguination by incision of the axillary or femoral arteries following anesthesia by intravenous injection of sodium pentobarbital. A sedative, Ketamine HCl for Injection, U.S.P. and Xylazine, was administered by intramuscular injection before animals were transported from the animal room to the necropsy area. In order to avoid autolytic change, a complete gross pathology examination of the carcass was conducted immediately on all animals which were euthanized. Food was withheld from all animals overnight before scheduled necropsy. No treatment related findings were detected during necropsy for any of the animals. Histopathological examination of any gross lesions was conducted. Again, no treatment related findings were observed. In addition, histopathological examination of the larynx, trachea, mainstem bronchi, lungs including bronchi was conducted. No treatment related abnormalities were observed.

Figure 2:
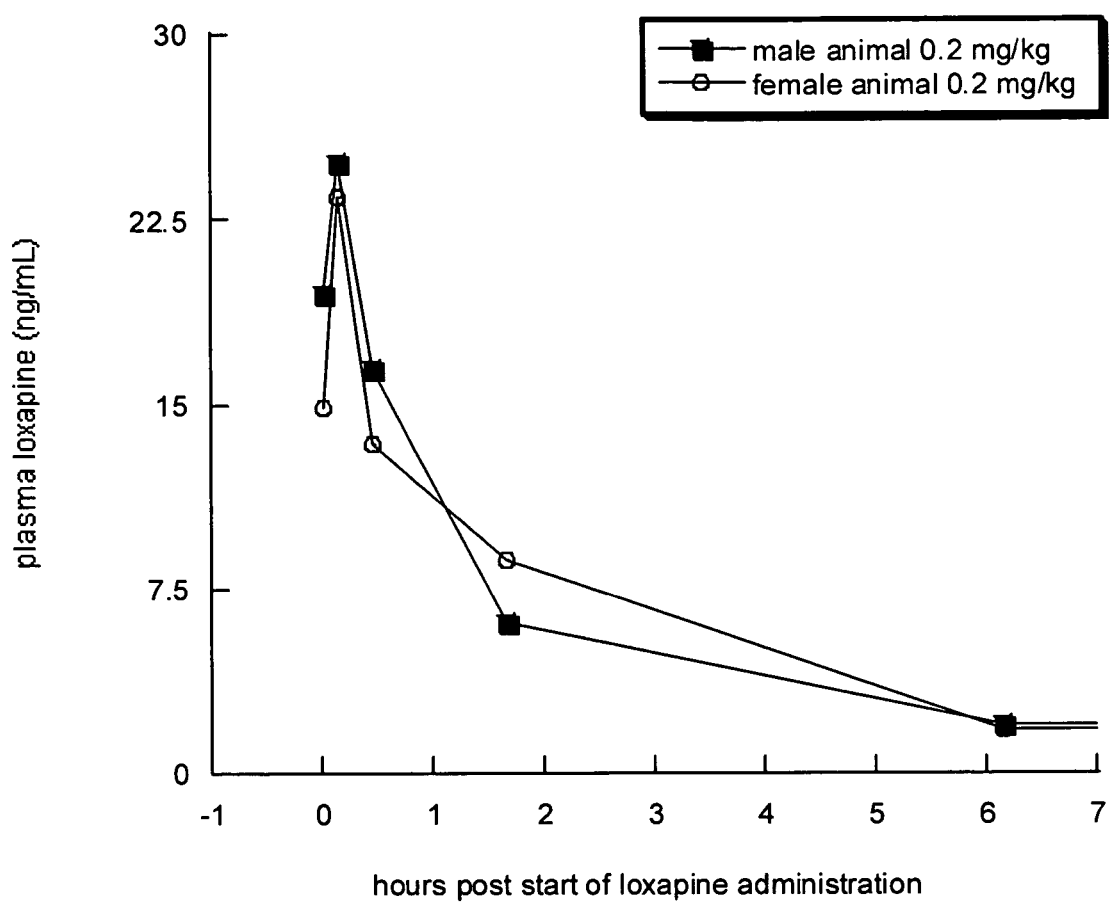
FIG. 2 is a plot showing plasma concentration (ng/mL) of loxapine hours post start of loxapine administration via inhalation at a dose of 0.2 mg/kg in beagle dogs.

On the first day of the repeat dose (5 day) portion of the study, plasma samples were collected for toxicokinetic analysis prior to dosing, 2 minutes after the onset of dosing, immediately after dosing, 20 minutes and 1, 3, 9 and 24 hours post dosing. Samples were stored at −80° C. until loxapine plasma concentration analysis. Loxapine plasma concentration can be measured using analytical methods well known in the art, such as LC/MS, LC/MS/MS, and/or GC/MS. Prophetic representative loxapine toxicokinetic data are provided in FIGS. 1 and 2. Note in these data that loxapine plasma concentration rise very rapidly after aerosol loxapine administration, with peak plasma concentration obtained within 2 minutes of end of drug inhalation. The rate of rise in loxapine plasma concentration is found to average at least 70 ng/mL/minute at the 2 mg/kg dose level over the first 2 minutes of dosing, and 20 ng/mL/minute at the 2 mg/kg dose level over the first 10 minutes of dosing. The rate of rise in loxapine plasma concentration is found to average at least 7 ng/mL/minute at the 0.2 mg/kg dose level over the first 2 minutes of dosing, and 2 ng/mL/minute at the 0.2 mg/kg dose level over the first 10 minutes of dosing. Therapeutic plasma levels of approximately at least 0.5 ng/mL, 1 ng/mL, 2 ng/mL, 4 ng/mL, 8 ng/mL, or even 15 ng/mL are obtained within 10 minutes, 5 minutes, and even within 2 minutes at both dose levels.

Prophetic Examples

Example 3

Phase I Clinical Trial of Loxapine Condensation Aerosol

A condensation aerosol generating handheld device as disclosed in U.S. patent application Ser. No. 10/633,876, filed Aug. 4, 2003 titled "Rapid-Heating Drug Delivery Article and Method of Use", is coated with loxapine so as to release a 0, 2.5 mg, 5 mg, or 10 mg (depending on coating thickness) of loxapine condensation aerosol over a period of less than 1 second following actuation of the device by patient inspiration.

Normal volunteers generally in the 18 to 45 year age range and not suffering from serious psychiatric, neurological, pulmonary, renal or cardiovascular disease are recruited to participate in the study, explained the potential risks of loxapine inhalation, and asked for their informed consent. Those consenting are enrolled in the study and an intravenous catheter is placed.

Volunteers are then given a handheld device. They may or may not be trained in appropriate breathing technique for use of the device prior to receiving the device. Minimally, each volunteer is instructed to exhale fully, then place the device in his or her lips and take a long, deep inhalation which is held for several seconds prior to exhaling. The volunteer then uses the device, receiving the prescribed quantity of loxapine condensation aerosol. The volunteer and the medical personnel conducting the study may be blinded as to the dose of drug, or as to whether the drug is replaced by placebo (i.e., a device loaded with 0 mg loxapine).

Venous blood samples are obtained approximately at 0.3, 1, 3, 10, 30, 60, 120, 240, 360, 500, 750, and 1000 minutes after dosing. Plasma drug concentrations are determined using established methods described in the literature for loxapine. These analyses reveal a $T_{max}$ of less than 10 minutes, with the $T_{max}$ generally occurring at the 3 minute sample or the 1 minute sample. Bioavailability of the condensation aerosol delivery is greater than 35%, and often greater than 55%.

The below table provides illustrative anticipated $C_{max}$ values at different doses:

| Dose | $C_{max}$ typically greater than | Most typical $C_{max}$ greater than |
|---|---|---|
| 2.5 mg | 2.5 ng/mL | 15 ng/mL |
| 5 mg | 5 ng/mL | 30 ng/mL |
| 10 mg | 10 ng/mL | 60 ng/mL |
| 20 mg | 20 ng/mL | 120 ng/mL |

Example 4

Phase II Clinical Trial of Loxapine for the Treatment of Acute Migraine Attacks

The study methodology is a double-blind, randomized, placebo-controlled dose-ranging trial. Healthy male and female subjects 18 to 65 years of age, inclusive, with a history of moderate to severe migraine headache by self-report (migraine with or without aura) with average frequency of 1-6 attacks per month during the past 3 months are recruited to participate in the study. Those subjects meeting entry criteria are enrolled and randomized to receive one of the following treatments: placebo, loxapine rapid delivery system ~1.25 mg, loxapine rapid delivery system ~2.5 mg, loxapine rapid delivery system ~5 mg, loxapine rapid delivery system ~10 mg. Higher loxapine doses may also be tested if found safe in a Phase I clinical trial. The loxapine rapid delivery system is a means of delivering loxapine to a migraine patient such that maximum plasma drug concentrations are obtained within 1 hour, 30 minutes, 15 minutes, 10 minutes, 5 minutes, or even 2 minutes or less. The condensation aerosol delivery system described above with respect to a Phase I clinical trial is one such system. Other rapid delivery systems include various durations of intravenous infusions or injections.

Immediately prior to receiving the treatment to which the patient has been randomized, the patient rates their severity of headache and nausea on a 4-point scale (0—absent, 1—mild, 2—moderate, 3—severe) and photophobic and phonophobia on a 2-point scale (Does light make your headache worse? 0—No, 1—Yes; Does noise make your headache worse? O—No, 1—Yes). Alternatively, an 11-point visual-analogue scale (0—none to 10—maximally severe) or other appropriate scale can be used. Subjects are asked to repeat these ratings at timepoints of 15 and 30 minutes following treatment, and also at 1, 2, 4, 8, 12 and 24 hours post treatment. Subjects are further asked for their global assessment of treatment efficacy (1—very poor to 5—very good) at 120 minutes and 24 hours post treatment. Concomitant medications, if any, are also recorded.

The groups receiving 5 mg and 10 mg of loxapine show a strong therapeutic effect of the drug within 1 hour. In particular, the severity of headache at 1 hour, and even 30 minutes, and sometimes even 15 minutes in the treated patients is markedly lower than prior to treatment. Comparison of placebo and 5 mg or 10 mg in terms of headache relief at 1 hour shows a marked advantage for the loxapine treated patients, as evidenced (assuming appropriately large sample size) by statistically significant (at the $p<0.05$ level) advantages for drug versus placebo in terms of lower migraine headache score, lower nausea score, less presence of photophobia and phonophobia, greater decrease in headache score from baseline headache score, greater percentage of patients with only mild or no headache, and greater percentage of patients with no headache. This advantage persists at 2 hours, 4 hours, 8 hours, and even 24 hours, unless the placebo-treated patients are provided rescue medication. Similar effects are seen with appropriately large samples at the 1.25 mg or 2.5 dose levels also, although sometimes appropriately large patient samples are difficult to acquire at those dose levels (because the effect is sometimes less strong, more patients are needed). Also, at the lower dose levels of 1.25 mg or 2.5 mg the drug sometimes requires a longer duration (e.g. 1 hour instead of 30 minutes) to be effective.

Example 5

Clinical Use of Loxapine for the Treatment of an Acute Migraine Attacks

A 35 year old woman in generally good health notes onset of moderate pain localizing to the right side of her head over approximately 10 minutes while at home. Over the next 10 minutes, the pain becomes more severe, characterized by throbbing. The woman recognizes this as a migraine headache, and also knows that for her such headaches, when untreated, tend to persist for at least a full day with nausea accompanying the headache pain and with the pain so severe as to render sleeping difficult or impossible. The woman turns down the lights in her living room to avoid the pain caused by bright light entering her eyes, and turns off the radio, because noise from the radio was worsening her headache pain. She takes a 25 mg loxapine tablet by mouth with a glass of water. Over the next 15 minutes, the headache pain begins to worsen, and the woman's stomach is mildly upset. However, over the following 1 hour, the headache pain diminishes slowly and the woman becomes increasingly tired. Her stomach no longer bothers her. She takes a brief nap and wakes up without any signs of headache. Light and sound are no longer bothersome. She eats a normal meal without stomach upset. The headache does not return over the next 72 hours, and no further medication is required.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A method for treating headache comprising administering to a subject in need of headache relief, an effective amount of a compound selected from the group consisting of loxapine, pharmaceutically acceptable salts of loxapine, and prodrugs of loxapine wherein 0.3 to 6.0 mg of loxapine is administered, or an amount of a salt or prodrug of loxapine is administered that produces in the subject a blood concentration of loxapine equivalent to the administration of 0.3 to about 6.0 mg of loxapine.

2. A method in accordance with claim 1, wherein said headache is a migraine headache.

3. A method in accordance with claim 1, wherein said headache is a cluster headache.

4. A method in accordance with claim 1, wherein said headache is a tension-type headache.

5. A method in accordance with claim 1, wherein said compound is administered by inhalation.

6. A method in accordance with claim 1, wherein said subject is human, said headache is a migraine headache, and said compound is administered by inhalation.

7. A method in accordance with claim 1, wherein the compound is formulated so as to result in a maximum blood level of loxapine within about 30 minutes from administration.

8. A method in accordance with claim 1, wherein the compound is formulated so as to result in a maximum blood level of loxapine within about 15 minutes from administration.

9. A method in accordance with claim 1, wherein the compound is formulated so as to result in a peak rate of increase in the blood level of loxapine of at least about 1 ng/ml/minute.

10. A method in accordance with claim 1, wherein the compound is formulated so as to result in a blood level of loxapine of at least about 5 ng/ml within about 15 minutes from administration.

11. A method in accordance with claim 1, wherein said compound is administered via inhalation using a rapid-heating drug delivery article or a thin-film drug delivery article.

12. A method in accordance with claim 1, wherein said compound is administered via an inhalation delivery device, wherein said compound is vaporized and condensed to provide at least 50% recovery of said compound in an aerosol, and wherein said aerosol contains less than about 5% by weight of compound degradation products.

13. A method in accordance with claim 12, wherein said compound is coated on a substrate in the delivery device as a film having a thickness between about 0.5 and 20 µm.

14. A method in accordance with claim 1, wherein said compound is administered in the form of an aerosol having a mass median aerodynamic diameter of between about 0.01 and about 3 µm.

15. A method in accordance with claim 1, wherein said compound is administered via a rapid heating drug delivery article, and wherein said compound is volatized from a compound composition film under conditions sufficient to provide an aerosol having at least 50% recovery of said compound and containing less than about 10% by weight of compound degradation products.

16. A method for treating headache pain in a subject comprising administering to said subject an effective amount of a compound selected from the group consisting of loxapine, pharmaceutically acceptable salts of loxapine and prodrugs of loxapine wherein 0.3 to 6.0 mg of loxapine is administered, or an amount of a salt or prodrug of loxapine is administered that produces in the subject a blood concentration of loxapine equivalent to the administration of 0.3 to about 6.0 mg of loxapine.

* * * * *